(12) United States Patent
Peakman (10) Patent No.: US 11,400,131 B2
(45) Date of Patent: Aug. 2, 2022

(54) MULTI-PEPTIDE COMPOSITION

(71) Applicant: King's College London, London (GB)

(72) Inventor: Mark Peakman, London (GB)

(73) Assignee: King's College London, London (GB)

( * ) Notice: Subject to any disclaimer, the term of this patent is extended or adjusted under 35 U.S.C. 154(b) by 1269 days.

(21) Appl. No.: 15/580,791

(22) PCT Filed: Jun. 10, 2016

(86) PCT No.: PCT/GB2016/051726
§ 371 (c)(1),
(2) Date: Dec. 8, 2017

(87) PCT Pub. No.: WO2016/198887
PCT Pub. Date: Dec. 15, 2016

(65) Prior Publication Data
US 2018/0221434 A1 Aug. 9, 2018

(30) Foreign Application Priority Data
Jun. 10, 2015 (GB) .................... 1510056

(51) Int. Cl.
| | | |
|---|---|---|
| *A61K 38/10* | (2006.01) | |
| *G01N 33/50* | (2006.01) | |
| *C07K 14/62* | (2006.01) | |
| *C12N 9/16* | (2006.01) | |
| *A61K 39/00* | (2006.01) | |
| *A61P 3/10* | (2006.01) | |
| *A61K 38/00* | (2006.01) | |
| *A61K 9/00* | (2006.01) | |

(52) U.S. Cl.
CPC .......... *A61K 38/10* (2013.01); *A61K 39/0008* (2013.01); *A61P 3/10* (2018.01); *C07K 14/62* (2013.01); *C12N 9/16* (2013.01); *G01N 33/5023* (2013.01); *G01N 33/5091* (2013.01); *A61K 9/0021* (2013.01); *A61K 38/00* (2013.01); *G01N 2800/042* (2013.01); *G01N 2800/52* (2013.01)

(58) Field of Classification Search
CPC ................... A61K 38/10; A61P 3/10
See application file for complete search history.

(56) References Cited

U.S. PATENT DOCUMENTS 7,049,292 B2 * 5/2006 Peakman ............... C07K 14/62
514/6.9
2005/0176637 A1 8/2005 Peakman
2007/0190045 A1 * 8/2007 Herold ............ A61K 39/39541
424/131.1

FOREIGN PATENT DOCUMENTS

| WO | 00/063702 A1 | 10/2000 |
| WO | 02/053106 A2 | 7/2002 |
| WO | 2005/073248 A1 | 8/2005 |

OTHER PUBLICATIONS

Celestino et al. "Rationale use of antioxidants in solid oral pharmaceutical preparations" Brazilian J. Pharm. Sci. 48:405-415. (Year: 2012).*
International Search Report issued in corresponding International Patent Application No. PCT/GB2016/051726 dated Aug. 23, 2016.
Written Opinion issued in corresponding International Patent Application No. PCT/GB2016/051726 dated Aug. 23, 2016.

* cited by examiner

*Primary Examiner* — Sudhakar Katakam
*Assistant Examiner* — Zachary J Miknis
(74) *Attorney, Agent, or Firm* — Morgan, Lewis & Bockius LLP (57) ABSTRACT

The invention relates to a specific peptide combination. The peptide combination may be present in a pharmaceutically acceptable composition. The peptide combination can be used in the therapy or prevention of Type 1 Diabetes (TID). The invention also relates to a method of diagnosing or determining treatment efficacy, the method utilising the specific peptide combination.

24 Claims, 6 Drawing Sheets
Specification includes a Sequence Listing.

MULTI-PEPTIDE COMPOSITION

SEQUENCE LISTING SUBMISSION VIA EFS-WEB

A computer readable text file, entitled "SequenceListing.txt," created on or about 30 Nov. 2017 with a file size of about 3 kb contains the sequence listing for this application and is hereby incorporated by reference in its entirety.

FIELD OF THE INVENTION

The invention relates to a peptide combination which can be used in the therapy or prevention of Type 1 Diabetes (T1D).

BACKGROUND TO THE INVENTION

Type 1 Diabetes (T1D) is an auto-immune disease characterised by metabolic dysfunction, most notably dysregulation of glucose metabolism, accompanied by characteristic long-term vascular and neurological complications. T1D is one of the most common autoimmune diseases, affecting one in 250 individuals in the US where there are approximately 10,000 to 15,000 new cases reported each year, and the incidence is rising. The highest prevalence of T1D is found in northern Europe.

T1D is characterised by absolute insulin deficiency, making patients dependent on exogenous insulin for survival. Prior to the acute clinical onset of T1D with symptoms of hyperglycaemia there is a long asymptomatic preclinical period, during which insulin-producing beta cells are progressively destroyed.

Beta cell autoantigens, macrophages, dendritic cells, B lymphocytes, and T lymphocytes have been shown to be involved in the pathogenesis of autoimmune diabetes. Beta cell autoantigens are thought to be released from beta cells and are processed and presented to T helper cells (CD4+ cells) by antigen-presenting cells. Naive CD4+ T cells can be activated by interleukin (IL)-12 released from antigen presenting cells. Beta cell antigen-specific CD8+ T cells are activated by the IL-2 produced by the activated CD4+ T cells, differentiate into cytotoxic T cells and are recruited into the pancreatic islets. These activated TH1 CD4+ T cells and CD8+ cytotoxic T cells are involved in the destruction of beta cells. IL-2 also activates B lymphocytes to secrete islet cell autoantibodies.

In recent years, several autoantigens against which islet cell autoantibodies are directed have been identified. These include the tyrosine phosphatase-related islet antigen 2 (IA-2), and insulin, pro-insulin (PI) and preproinsulin.

Once initiated, treatment with injections of synthetic insulin is required for life since beta cells do not re-generate. Once established, diabetes is a major burden to the patient, to the patient's family, and to society. Although modern dosages, preparations and delivery systems for insulin can maintain blood glucose within reasonable limits, over several years complications of the disease inevitably occur. The commonest severe complications of diabetes are kidney failure, blindness, and loss of nerve function. The life span of a patient with diabetes is reduced by an average of 10 years. In light of this background, it is important to consider new means of treating or preventing T1D. T-cell IA-2 epitopes have been identified in Honeyman M, et al. (Honeyman M, et al. Molecular Medicine 1998; 4: 231-239), Lohmann T, et al. (Lohmann T, et al. Exp Clin Endocrinol Diabetes 1999; 107 (3): 166-71), McLaughlin K A, et al. (McLaughlin K A, et al. J Immunol 2014; 193: 4448-56) and Weenink S M, et al. (Weenink S M, et al., J Autoimmun 2009; 33:147-54. PI and/or IA-2 peptides are also disclosed in U.S. Pat. No. 7,049,292, WO2005/073248, WO00/63702 and WO2009/004315. However, the present invention utilises a novel combination of key epitopes from both PI and IA-2, and/or a specific administration regime, which demonstrate superior performance of antigen-specific immunotherapy in order to limit the PI/IA-2 autoimmunity that is characteristic of T1D.

SUMMARY OF THE INVENTION

In a first aspect of the invention, there is provided a peptide combination comprising:
  a peptide having the amino acid sequence of SEQ ID NO: 1;
  a peptide having the amino acid sequence of SEQ ID NO: 2;
  a peptide having the amino acid sequence of SEQ ID NO: 3;
  a peptide having the amino acid sequence of SEQ ID NO: 4;
  a peptide having the amino acid sequence of SEQ ID NO: 5; and
  a peptide having the amino acid sequence of SEQ ID NO: 6.

SEQ ID NO: 1 is a fragment of IA-2, comprising residues 718-736.

SEQ ID NO: 2 is a fragment of IA-2, comprising residues 752-775.

SEQ ID NO: 3 is a fragment of IA-2, comprising residues 855-867.

SEQ ID NO: 4 is a fragment of PI, comprising residues C13-C32.

SEQ ID NO: 5 is a fragment of PI, comprising residues C19-A3.

SEQ ID NO: 6 is a fragment of PI, comprising residues C22-A5.

The inventor has surprisingly found that this peptide combination is superior at limiting anti-PI and anti-IA-2 autoimmunity compared to smaller numbers of peptides and alternative peptide combinations. Surprisingly, it has also been demonstrated that different combinations of IA-2 peptides offer different effects in limiting PI autoimmunity. The presently claimed peptide combination has a superior performance when compared with other peptide combinations. In particular, the peptide combination of the present invention demonstrates trans-antigen linked suppression which can be of considerable benefit to patients when exploited therapeutically. It allows a limited number of peptides, from a limited number of auto-antigens, to be used to target the multiple different autoimmune responses which play a role in T1D.

As herein described the term "peptide" refers to any peptide comprising amino acids joined to each other by peptide bonds or modified peptide bonds, i.e., peptide isosteres. The peptide generally will contain naturally occurring amino acids but may include amino acid sequences modified either by natural processes, such as post-translational processing, or by chemical modification techniques which are well known in the art. Such modifications are well described in basic texts. Modifications can occur anywhere in a peptide, including the peptide backbone, the amino acid side-chains and the amino or carboxyl termini. It will be appreciated that the same type of modification may be present in the same or varying degrees at several sites in a given peptide. Also, a given peptide may contain many types of modifications.

In a preferred embodiment, the peptide combination does not comprise other peptides from IA-2 or PI.

Preferably, the claimed peptide combination comprises the exact sequences of the present invention and not longer fragments of, or the full length IA-2 or PI.

It will be apparent to one skilled in the art that the peptide combination of the present invention may comprise non-peptide components, such as excipients as discussed further below, but that it may not comprise any additional peptides, in particular peptides from IA-2 or PI.

Preferably, the peptides which make up the peptide combination are isolated peptides. The term "isolated" means that the peptide is removed from its original environment. For example, a peptide present in a living animal is not isolated, but the same peptide, or a fragment of such a peptide, separated from some or all of the coexisting materials in the natural system, is isolated. Such peptides could be part of a vector and/or peptides could be part of a composition, and still be isolated in that such vector or composition is not part of its natural environment.

In a preferred embodiment, the peptide combination consists of:
a peptide having the amino acid sequence of SEQ ID NO: 1;
a peptide having the amino acid sequence of SEQ ID NO: 2;
a peptide having the amino acid sequence of SEQ ID NO: 3;
a peptide having the amino acid sequence of SEQ ID NO: 4;
a peptide having the amino acid sequence of SEQ ID NO: 5; and
a peptide having the amino acid sequence of SEQ ID NO: 6.

In this preferred embodiment, the peptide combination only comprises the recited peptides having the specific recited sequences.

A second aspect of the invention relates to a pharmaceutically acceptable composition comprising the peptide combination of the present invention and one or more pharmaceutically acceptable excipients.

Preferably the pharmaceutical composition comprising cysteine. The presence of free cysteine within the composition stabilises any tendency for the peptides of the peptide combination to form inter-chain disulphide bonds and thus precipitate. The pharmaceutical composition may comprise 1 to 5 mg of L-cysteine per 2 mg of peptide combination, preferably 2 to 4 mg of L-cysteine per 2 mg of peptide combination and most preferably, 2.5 mg of L-cysteine per 2 mg of peptide combination.

The pharmaceutical composition may be for human or animal usage in human and veterinary medicine and will typically comprise one or more suitable excipients. Acceptable excipients for therapeutic use are well known in the pharmaceutical art, and are described, for example, in Remington's Pharmaceutical Sciences, Mack Publishing Co. (A. R. Gennaro edit. 1985). The choice of pharmaceutical excipient can be selected with regard to the intended route of administration and standard pharmaceutical practice. The pharmaceutical compositions may comprise as, or in addition to, the excipient any suitable binder, lubricant, suspending agent, coating agent or solubilising agent.

Preservatives, stabilizers and dyes may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered parenterally in which the composition is formulated in an injectable form, for delivery, by, for example, an intravenous, intradermal, intramuscular, subcutaneous or intraperitoneal route. For parenteral administration, the compositions may be best used in the form of a sterile aqueous solution which may contain other substances, for example enough salts or monosaccharides to make the solution isotonic with blood. The composition may also be formulated to be administered by oral or topical routes, including nasally, orally or epicutaneously. Preferably the composition is formulated to be delivered by an intradermal route.

Intradermal administration routes include any dermal-access means, for example, using microneedle-based injection and infusion systems (or other means to accurately target the intradermal space), needleless or needle-free ballistic injection of fluids or powders into the intradermal space, Mantoux-type intradermal injection, enhanced iontophoresis through microdevices, and direct deposition of fluid, solids, or other dosing forms into the skin, including the use of patches to deposit the composition onto the skin.

Typically, a physician will determine the actual dosage which will be most suitable for an individual subject and it will vary with the disease, age, weight and response of the particular patient. The appropriate dosage for humans can be determined by one skilled in the art, for example using body surface area (BSA) normalisation. For example, the pharmaceutical composition may comprise about 0.1 μg to 15 mg total peptide per single dose, preferably 1 μg to 12 mg total peptide per single dose. In one preferred embodiment, 240 μg (1 μg dose BSA normalized for a 60 kg adult human) of total peptide per single dose is administered with the peptides present in an equimolar ratio. In another preferred embodiment, 12 mg of total peptide per single dose is administered with the peptides present in an equimolar ratio.

In a preferred embodiment, the composition comprising the peptide combination of the present invention is administered at least once per month, preferably once every 1 to 4 weeks for four administrations.

In one embodiment, the composition comprising the peptide combination of the present invention is administered at least once per month, preferably once every 2 to 4 weeks for four administrations.

In another embodiment, the composition comprising the peptide combination of the present invention is administered at least once per month, preferably once per week for four weeks.

The pharmaceutical composition may also comprise tolerance-promoting adjuvants and/or tolerance promoting cells. Tolerance promoting adjuvants include IL-10, recombinant cholera toxin B-subunit (rCTB), ligands for Toll-like receptor 2, as well as biologics and monoclonal antibodies that modulate immune responses, such as anti-CD3 and co-stimulation blockers, which may be co-administered with the peptide combination. Tolerance promoting cells include immature dendritic cells and dendritic cells treated with vitamin D3, (1alpha,25-dihydroxy vitamin D3) or its analogues. Preferably one or more of the peptides of the peptide combination of the present invention are conjugated to the surface of a dendritic cell treated with vitamin D3 or its analogues. Preferably all of the peptides of the peptide combination of the present invention are conjugated to the surface of a dendritic cell treated with vitamin D3 or its analogues.

A third aspect of the invention relates to the pharmaceutically acceptable composition of the present invention for use in therapy.

A fourth aspect of the invention relates to the pharmaceutically acceptable composition of the present invention for use in the treatment or prevention of Type 1 Diabetes (T1D).

When T1D is "treated", this means that one or more clinical manifestations of T1D are ameliorated. It does not mean that the symptoms of T1D are completely remedied so that they are no longer present in the patient, although in some methods, this may be the case. "Treatment" results in one or more of the symptoms of T1D being less severe than before treatment.

A fifth aspect of the invention relates to the pharmaceutically acceptable composition of the present invention for use in the manufacture of a medicament for the treatment or prevention of Type 1 Diabetes (T1D).

A sixth aspect of the invention relates to a method of treatment or prevention of Type 1 Diabetes (T1D) in which the pharmaceutically acceptable composition of the present invention is administered to a patient with T1D or a non-diabetic individual identified as being at high-risk of T1D.

Preferably the pharmaceutically acceptable composition of the present invention is administered to a patient who has beta cell mass remaining.

A seventh aspect of the invention relates to a kit for the treatment or prevention of Type 1 Diabetes (T1D) which comprises the peptide combination of the present invention.

An eighth aspect of the invention relates to a method of diagnosis or determining treatment efficacy comprising: (a) providing CD4 lymphocytes from an individual suspected of having or being susceptible to T1D; (b) providing a population of Antigen Presenting Cells (APCs) which bear on their surface a class II MHC molecule of an allele identical to one expressed by said individual, the population of APCs having been contacted with the peptide combination of the present invention and the class II MHC molecule being bound to one or more of the peptides of the peptide combination of the present invention; or (c) providing a soluble peptide-HLA multimer reagent comprising class II MHC molecules of an allele identical to one expressed by said individual, the MHC molecules having been bound to one or more peptides of the peptide combination of the present invention; (d) contacting the population of APCs of (b) or the peptide-HLA multimer of (c) with the CD4 lymphocytes of (a); and (e) determining whether the CD4 lymphocytes recognize the class II MHC-bound peptide, as an indication that the individual has, or is, susceptible to T1D.

Such APC can be B-lymphocytes, monocytes, macrophages, or dendritic cells, or whole peripheral blood mononuclear cells (PBMC). APC can also be immortalised cell lines derived from B-lymphocytes, monocytes, macrophages, or dendritic cells. Where the subjects are humans, the APC can also be T cells since human T cells are capable of expressing class II MHC molecules. The method further comprises administering the peptide combination of the present invention to the individual if the CD4 lymphocytes recognise the class II MHC-bound peptide.

A ninth aspect of the invention relates to a peptide combination comprising:
  a peptide having the amino acid sequence of SEQ ID NO: 4;
  a peptide having the amino acid sequence of SEQ ID NO: 5; and
  a peptide having the amino acid sequence of SEQ ID NO: 6 for use in the treatment or prevention of Type 1 Diabetes (T1D) wherein the combination is for administration at least once per month, preferably once every 1 to 4 weeks for four administrations.

In one embodiment, the composition comprising the peptide combination of the present invention is administered at least once per month, preferably once every 2 to 4 weeks for four administrations.

In another embodiment, the composition comprising the peptide combination of the present invention is administered at least once per month, preferably once per week for four weeks.

"Wherein the composition is for administration" means that the combination is administered. Preferably the peptide combination is for administration at a dosage of 240 µg or 12 mg total peptide with the peptides present in an equimolar ratio.

Preferably the peptide combination is formulated as a pharmaceutically acceptable composition which includes one or more pharmaceutically acceptable excipients. Preferably the composition is formulated to be delivered by parenteral, oral or topical routes, including intravenous, intradermal, intramuscular, subcutaneous, intraperitoneal, nasal, oral or epicutaneous routes and more preferably, the composition is formulated to be delivered by an intradermal route.

A tenth aspect of the invention relates to a method of treatment or prevention of Type 1 Diabetes (T1D) in which a peptide combination comprising:
  a peptide having the amino acid sequence of SEQ ID NO: 4;
  a peptide having the amino acid sequence of SEQ ID NO: 5; and
  a peptide having the amino acid sequence of SEQ ID NO: 6 is administered to a patient with T1D or a non-diabetic individual identified of being at high-risk of T1D at least once per month, preferably once every 1 to 4 weeks for four administrations.

In one embodiment, the composition comprising the peptide combination of the present invention is administered at least once per month, preferably once every 2 to 4 weeks for four administrations.

In another embodiment, the composition comprising the peptide combination of the present invention is administered at least once per month, preferably once per week for four weeks.

Preferably the combination is administered at a dosage of 240 µg or 12 mg total peptide with the peptides present in an equimolar ratio.

Preferably the peptide combination is formulated as a pharmaceutically acceptable composition which includes one or more pharmaceutically acceptable excipients. Preferably the composition is formulated to be delivered by parenteral, oral or topical routes, including intravenous, intradermal, intramuscular, subcutaneous, intraperitoneal, nasal, oral or epicutaneous routes and more preferably, the composition is formulated to be delivered by an intradermal route.

A skilled person will appreciate that all aspects of the invention, whether they relate to, for example, the peptide composition, its use, the pharmaceutically acceptable composition or a method of treatment are equally applicable to all other aspects of the invention. In particular, aspects of the peptide combination for example, may have been described in greater detail than in other aspects of the invention, for example, the use of peptide combination. However, the skilled person will appreciate where more detailed information has been given for a particular aspect of the invention, this information is generally equally applicable to other aspects of the invention.

DETAILED DESCRIPTION OF THE INVENTION

The invention will now be described in detail by way of example only with reference to the figures in which:

FIG. 4 shows that treating mice with a combination of 3 PI peptides is more effective than treatment with a single PI peptide. In brief, tolerance to proinsulin was breached in mice by subcutaneous immunisation with 100 µg proinsulin protein emulsified in CFA and treatment with intraperitoneal pertussis toxin immediately and 1 day after immunisation. Mice then received 4 weekly intradermal treatments of 10 µg control-PI or proinsulin mono/multi-PI (C13-32 (SEQ ID NO: 4); C19-A3 (SEQ ID NO: 5); C22-A5 (SEQ ID NO:6)), before subcutaneous immunisation with 100 µg proinsulin protein emulsified in IFA to boost the ongoing autoimmune response (A). Lymph nodes (LNs) were harvested 7 days later and LN cell suspensions were cultured with or without proinsulin protein or peptide (C13-32; C19-A3; C22-A5) for 48 hours in vitro. Proliferation of CD4$^+$ T cells and IFN-γ production were analysed by CFSE dilution at 96 hours (B) and ELISA at 48 hours (C) in response to in vitro stimulation with 50 µg/mL proinsulin protein and 10 µg/mL peptides (C13-32; C19-A3; C22-A5). Serum levels of proinsulin specific IgG1 were measured at day 42 (D). Percentages of proliferating CD3$^+$CD4$^+$CD25$^{high}$FoxP3$^+$ Tregs were measured by flow cytometry in LN cultures at day 42 (E). Data are representative of three independent experiments. *p<0.05, p<0.01, *p<0.001; Statistical significance was determined by one-way ANOVA or Student's t test. 15 mice per group in B and C; 5 mice per group D-F.

FIG. 5 shows that an increased frequency of low dose multi-PI is more effective than a higher dose or fewer treatments at reversing the break of tolerance to whole proinsulin. Tolerance to proinsulin was breached in mice by subcutaneous immunisation with 100 µg proinsulin protein emulsified in CFA and treatment with intraperitoneal pertussis toxin immediately and 1 day after immunisation. Mice then received 4 or 2 weekly intradermal treatments of 10 µg or 1 µg consisting of 3 proinsulin peptides (C13-32; C19-A3; C22-A5) or control HA peptide, before subcutaneous immunisation with 100 µg proinsulin protein emulsified in IFA to boost the ongoing autoimmune response (A). LNs were harvested at day 42 and LN cells were cultured with or without proinsulin protein or peptide (C13-32; C19-A3; C22-A5) for 48 hours in vitro. Proliferation and cytokine production were analysed by thymidine incorporation and ELISA and the mean±SEM proliferation in response to 50 µg/mL proinsulin (B) and IFN-γ production in response to 50 µg/mL proinsulin (C) or 10 µg/mL proinsulin peptides, in DLN cultures is shown. Percentage of proliferating CD3$^+$CD4$^+$CD25$^{high}$FoxP3$^+$ Tregs was measured by flow cytometry in LN cultures at day 42 (E). Serum levels of proinsulin specific IgG1 were measured at day 42 (F). Data are representative of at least two independent experiments. *p<0.05, p<0.01, *p<0.001; Statistical significance was determined by one-way ANOVA or Student's t test. 6 mice per group.

FIG. 6 shows that treatment with 3 PI peptides enhances antigen specific regulation. Tregs from mice treated with proinsulin multi-PI have enhanced proinsulin specific suppressor activity compared to control-PI treated mice. Tolerance to proinsulin was breached in mice by subcutaneous immunisation with 100 µg proinsulin protein emulsified in CFA and treatment with intraperitoneal pertussis toxin immediately and 1 day after immunisation. Mice then received 4 weekly intradermal treatments of 1 µg PI consisting of 3 proinsulin peptides (C13-32; C19-A3; C22-A5) or control HA peptide, before subcutaneous immunisation with 100 µg proinsulin protein emulsified in IFA to boost the ongoing autoimmune response (A). LNs were harvested at day 42 and CD4$^+$CD25$^{high}$ Tregs were isolated and co-cultured, at varying concentrations, with CFSE labelled responder T cells from mice immunised with proinsulin/CFA. Cells were co-cultured in the presence of αCD3αCD28 dyna-beads (B) or proinsulin protein (C) and proliferation of responder CD4$^+$ T cells was calculated by measuring CFSE dilution by flow cytometry at 96 hours. Mean±SEM proliferation of CFSE labelled responder cells in response to 50 µg/mL proinsulin in the presence of decreasing concentrations of CD4$^+$ CD25$^{high}$ Tregs from either HA- or proinsulin-PIT treated mice (D). Statistical significance was determined by one-way ANOVA or Student's t test. *p<0.05, **p<0.01, 15 mice per group (pooled lymph nodes).

EXAMPLE 1

Generation of a Mouse Model of Diabetes-Relevant Autoimmunity via Induction of Pro-Insulin-Specific/IA-2-Specific Autoreactivity B6.129S2-H2-Ab1$^{tm1Gru}$ Tg (HLA-DRA/H2-Ea,HLA-DRB1*0401/H2-Eb) 1Kito mice (HLA-DR4-Tg) (1) were imported from Taconic, USA and were used in all experiments. All animals were specified pathogen free and maintained under standard conditions at King's College London Biological Services Unit in accordance with Home Office Regulations.

Mice were challenged subcutaneously at the tail base with 100 µg whole recombinant human pro-insulin protein (Biomm, Brazil) and/or recombinant human insulinoma-associated antigen-2 (IA-2; Proteogenix) emulsified in Complete Freund's Adjuvant (CFA, Sigma-Aldrich). Mice were treated with 200 ng pertussis toxin (PTX, Sigma-Aldrich) delivered via the intraperitoneal cavity at the time of immunisation and 1 day later. When testing peptide immunotherapy, autoimmune responses were further boosted with 100 µg of autoantigen (pro-insulin and/or IA-2) emulsified in Incomplete Freund's Adjuvant (IFA, Sigma-Aldrich) subcutaneously at the tail base 7 days after the last peptide therapy treatment. Evidence for the induction of pro-insulin and IA-2-specific autoimmunity was obtained by testing recall responses to pro-insulin or IA-2 to demonstrate T-cell proliferation and T-cell inflammatory cytokine production.

Figure 2:
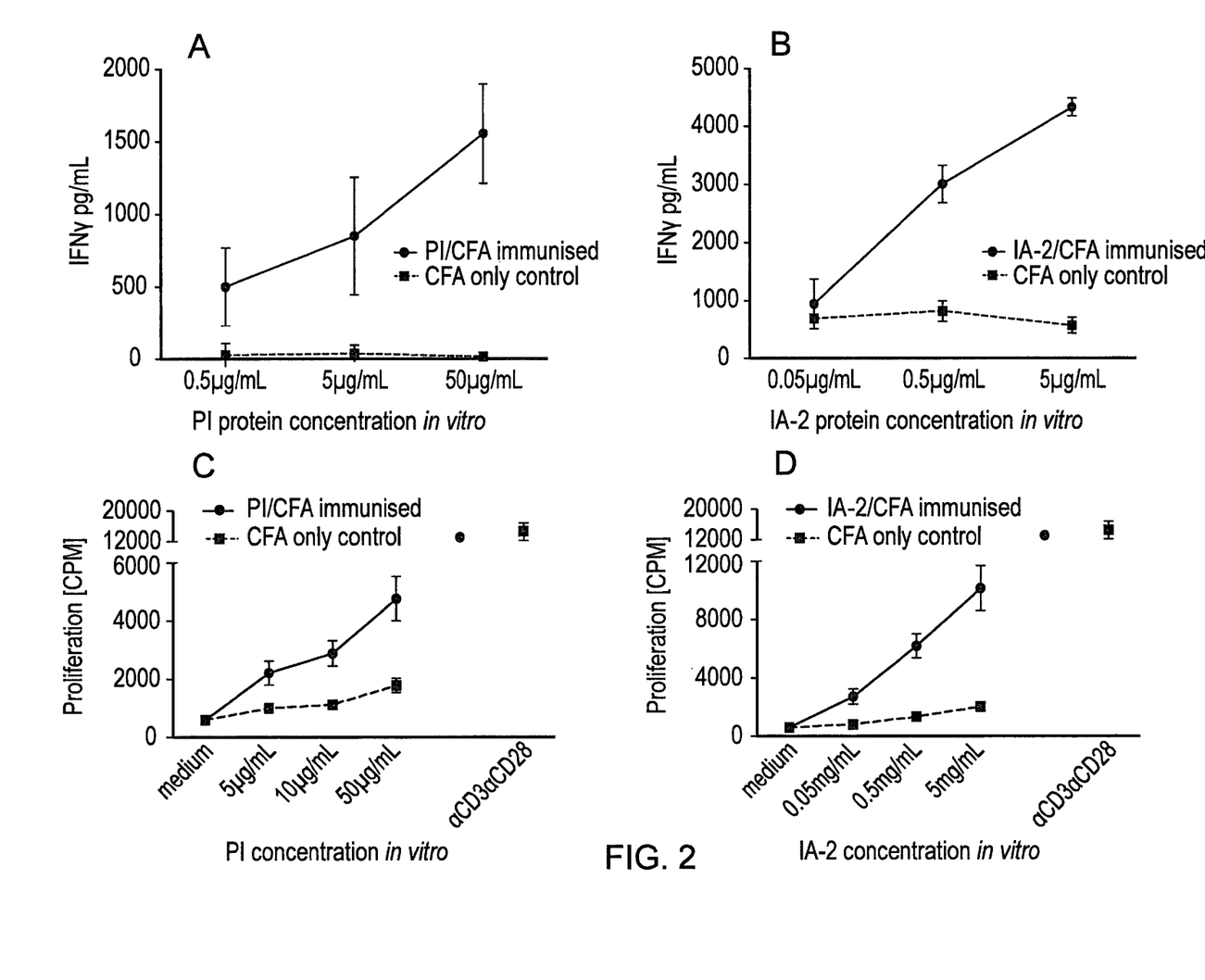
FIG. 2 shows the results of T cell proliferation as a read-out of PI- and IA-2-specific autoimmunity following immunisation with multi-peptide compositions to derive a preclinical model of diabetes-related autoimmunity.

The graphs of FIG. 2 show pro-inflammatory cytokine production against autoantigens proinsulin (PI) and IA-2 (panels A and B, respectively) and T cell proliferation (panels C and D, respectively) after immunization of humanized mice (HLA-DR4 Tg: mice transgenic for the human peptide presenting molecule HLA-DR4) with these autoantigens in CFA with pertussis toxin (PTX) adjuvant. It is well established that proliferation and pro-inflammatory cytokine production by T cells in response to these autoantigens is a characteristic of human Type 1 diabetes. Therefore these data indicate that the HLA-DR4 Tg mouse manipulated as shown can recapitulate autoimmune features of human disease.

EXAMPLE 2

Measuring Pro-Insulin and IA-2 Specific T Cell Proliferation, Inflammatory Cytokine Production and Induction of Proliferating Regulatory T cells (Treg) in Mice Draining lymph nodes (DLNs) were homogenized using a BD Cell Strainer (70 μm). Cells were washed in RPMI and re-suspended at $2.5 \times 10^6$ cells/ml in RPMI containing 0.5% autologous mouse serum. $2.5 \times 10^5$ cells were added to each well of a U bottom plate. Cells were re-stimulated with medium alone, α-CD3/α-CD28 dynabeads (Invitrogen) as a positive control stimulus or with pro-insulin protein or IA-2. At 48 hours supernatants were removed for cytokine analysis and 0.5 mCi/well tritiated thymidine [$^3$H] was added. The cells were harvested 18 hours later using a MicroBeta Trilux machine (Perkin Elmer). IFN-γ and IL-10 levels were measured in culture supernatants taken at 48 hours using a ready-SET-Go kit (ebiosciences) in accordance with manufacturer's guidelines.

Flow cytometry was performed according to standard protocol. Antibodies (Abs) (anti-CD4-PerCP, anti-FoxP3-APC, anti-CD3-PE, anti-CD25-FITC, anti-ki67-Pacific Blue (all eBioscience, UK), anti-CD11c-PE Cy7, anti-PDL1-PE, anti-CD86-FITC, anti-HLA-APC (all BD bioscience), were added to each sample at a dilution of 1:100. Intracellular staining was carried out using a standard kit and according to manufacturer's guidelines (Biolegend). Samples were analysed using a FACSCanto III flow cytometer equipped with a 405-nm Violet laser, a 488-nm Argon laser and a 635-nm red diode laser (BD Bioscience) and FlowJo software. Lymphocytes were first identified according to size and granularity using forward and side scatter parameters. CD4$^+$ T cells were next identified on the basis of CD3 and CD4 expression. Regulatory T cells were characterized on the basis of high CD25 expression and FoxP3 expression. Finally, proliferating regulatory CD3$^-$CD4$^-$FoxP3$^+$ CD25$^{high}$ T cells were identified on the basis of up-regulation of the nuclear protein, Ki67.

EXAMPLE 3

Pro-Insulin Specific Regulation

Tolerance to proinsulin was breached in mice as previously described. Mice then received 4 weekly intradermal treatments of 1 μg control-PI or proinsulin multi-PI (comprising equimolar amounts of C13-22, C19-A3 and C22-A5) before the ongoing autoimmune response to proinsulin was boosted by subcutaneous injection of proinsulin/IFA. Lymph nodes were removed and CD4$^+$ T cells were isolated by negative selection using a CD4 T cell isolation kit (Miltenyi Biotec, Germany). Cells were then stained with anti-CD25-FITC (ebioscience) and CD4$^-$ CD25$^{high}$ suppressor T cells were isolated by fluorescence-activated cell sorting (FACS) using a BD FACSAria. esponder cells from proinsulin/CFA immunised mice were labelled with CFSE as previously described and co-cultured with CD4$^+$ CD25$^{high}$ T cells for 96 hours with medium alone, α-CD3α-CD28 dynabeads or proinsulin protein. Proliferation of responder cells (corresponding to CFSE loss) was measured by flow cytometry. % Suppression was calculated by:

$$\frac{CFSE \text{ dilution of } Tresp - CFSE \text{ dilution of } Tresp:Treg}{CFSE \text{ dilution of } Tresp} \times 100$$

EXAMPLE 4

Identification of Optimal IA-2 Sequences in Human T1D Patients

Detection of interferon (IFN)-γ by CD4$^+$ T cells in response to peptide stimulation was carried out using an enzyme-linked immunospot (ELISPOT) assay that has significant discriminative ability for type 1 diabetes in blinded proficiency testing, as previously described (Arif, S. et al. J Clin Invest 2004; 113: 451-463 and Herold, K. C. et al. Diabetes 2009; 58: 2588-2595). Data are expressed as the mean number of spots per triplicate and compared with the mean spot number in the presence of diluent alone (stimulation index; SI). A response is considered positive when the SI is ≥3 using cut-offs determined using receiver-operator characteristic plots as previously described (Arif, S. et al. J Clin Invest 2004; 113: 451-463).

Figure 1A:
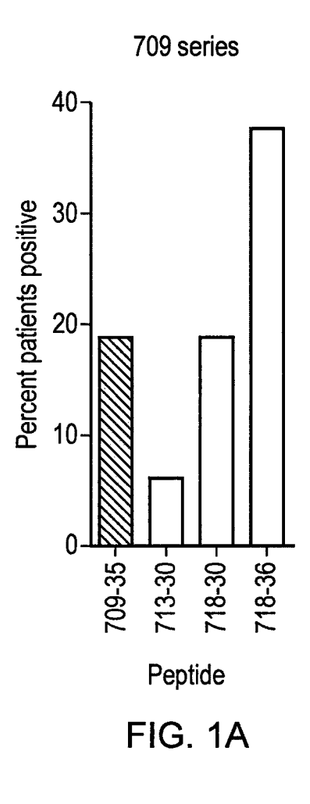
FIG. 1 shows the results of 3 parental sequences shown with cross-hatching, and compared with shorter nested sequence peptides to show the percentage of T1D patients responding, using production of interferon-γ as the read-out, detected by enzyme-linked immunospot.
Figure 1B:
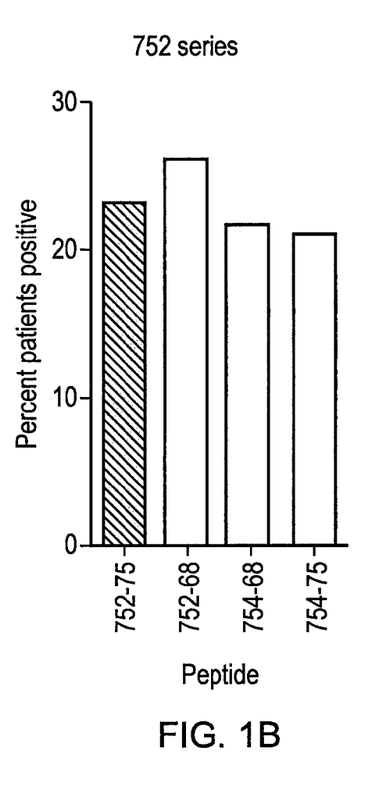
Figure 1C:
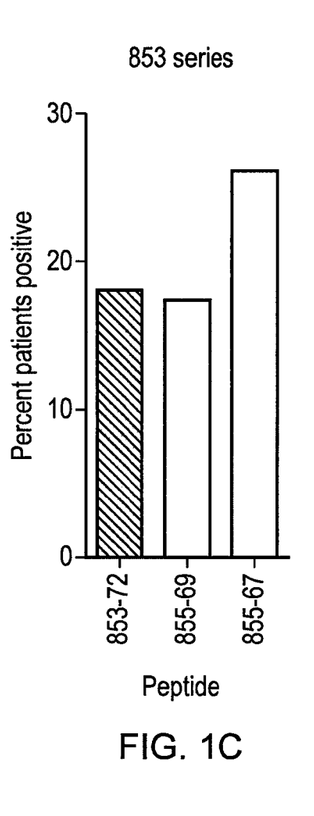

FIG. 1 shows the proportion (as %) of Type 1 diabetes patients responding to epitopes nested within a specific peptide series that we identified by elution (See Peakman M, et al. J Clin Invest 1999; 104:1449-57). The results are shown for 3 parental sequences (cross-hatched), and these are compared with shorter nested sequence peptides. Responses represent IFN-γ production by peripheral blood mononuclear cells cultured with each peptide, as detected using an enzyme-linked immunospot assay.

FIG. 1 illustrates the preferential sequences within the 709 series (718-36) and 853 series (855-67). None of the nested peptides for the 752 series is evidently superior.

EXAMPLE 5

Peptide Combinations

Several proinsulin (PI) and IA-2 peptide combinations were selected for evaluation as optimal in inducing immune regulation. See Table 1 below.

TABLE 1

Peptide cocktails used in Peptide Immunotherapy treatment

| Control | Group 1 | Group 2 | Group 3 | Group 4 |
|---|---|---|---|---|
| Filtered Sterile Water | IA2 718-36 (SEQ ID NO: 1) IA2 752-75 (SEQ ID NO: 2) | IA2 718-30 (SEQ ID NO: 7) IA2 752-75 | IA2 709-32 (SEQ ID NO: 9) IA2 752-75 | IA2 709-36 (SEQ ID NO: 11) IA2 752-75 |

TABLE 1-continued

Peptide cocktails used in Peptide Immunotherapy treatment

| Control | Group 1 | Group 2 | Group 3 | Group 4 |
|---|---|---|---|---|
| | IA2 855-67 (SEQ ID NO: 3) | IA2 855-69 (SEQ ID NO: 8) | IA2 856-70 (SEQ ID NO: 10) | IA2 853-72 (SEQ ID NO: 12) |
| | PI C13-32 (SEQ ID NO: 4) | PI C13-32 | PI C13-32 | PI C13-32 |
| | PI C19-A3 (SEQ ID NO: 5) | PI C19-A3 | PI C19-A3 | PI C19-A3 |
| | PI C22-A5 (SEQ ID NO: 6) | PI C22-A5 | PI C22-A5 | PI C22-A5 |

SEQ ID NO: 7 is a fragment of IA-2, comprising residues 718-730.

SEQ ID NO: 8 is a fragment of IA-2, comprising residues 855-869.

SEQ ID NO: 9 is a fragment of IA-2, comprising residues 709-732.

SEQ ID NO: 10 is a fragment of IA-2, comprising residues 856-870.

SEQ ID NO: 11 is a fragment of IA-2, comprising residues 709-736.

SEQ ID NO: 12 is a fragment of IA-2, comprising residues 853-872.

EXAMPLE 6

A Specific Six Peptide Combination is More Efficacious in Limiting Pro-Insulin and IA-2 Autoimmunity than Several Other Trialled Combinations HLA-DR4 transgenic (humanised) mice are rendered "autoimmune", by immunisation with strong adjuvants and PI/IA-2, to induce an inflammatory response to PI and IA-2 as described above. The inflammatory response includes T cell proliferation and inflammatory cytokine production, major hallmarks of autoimmune (Type 1) diabetes in man. Mice were assigned to treatment groups with the peptide cocktails or control as shown in Table 1.

Autoimmune responses against PI and IA-2 were induced in B6.129S2-H2-Ab1$^{tm1Gru}$ Tg (HLA-DRA/H2-Ea,HLA-DRB1*0401/H2-Eb) 1Kito mice (HLA-DR4-Tg) as described in Example 1 above. To examine the effects of different combinations of peptides administered as peptide immunotherapy on the induced autoimmune response, the peptide combinations shown in Table 1 or control (water for injection) were delivered in 100 μl sterile PBS by intradermal injection (10 μg total peptide content per injection, with the peptides at an equimolar ratio) over the abdomen, once weekly for 4 weeks. Autoimmune responses to PI and IA-2 were tested 7 days later by examining proliferation and cytokine production of lymph node cells against PI and IA-2 as described in Example 2.

Mice treated with the control will have robust T cell proliferation and inflammatory cytokine responses. Where therapy is effective, these responses will be significantly reduced.

Results are expressed as mean±standard error of mean (SEM). Gaussian distribution was confirmed by D'Agostino & Pearson omnibus normality test prior to significance being determined by one-way ANOVA or Student's t test. A value of $p<0.05$ was regarded as significant.

FIG. 3 represents recall proliferation responses to PI (panel A) and IA-2 (panel B) in vitro of lymph node cells obtained from HLA-DR4 Tg mice that have been rendered autoimmune against PI and IA-2 by immunisation. Mice have then been treated with control or one of the peptide combinations specified in Table 1. The data in FIG. 3 are shown as means (SEM) from n=8 per group.

Figure 3A:
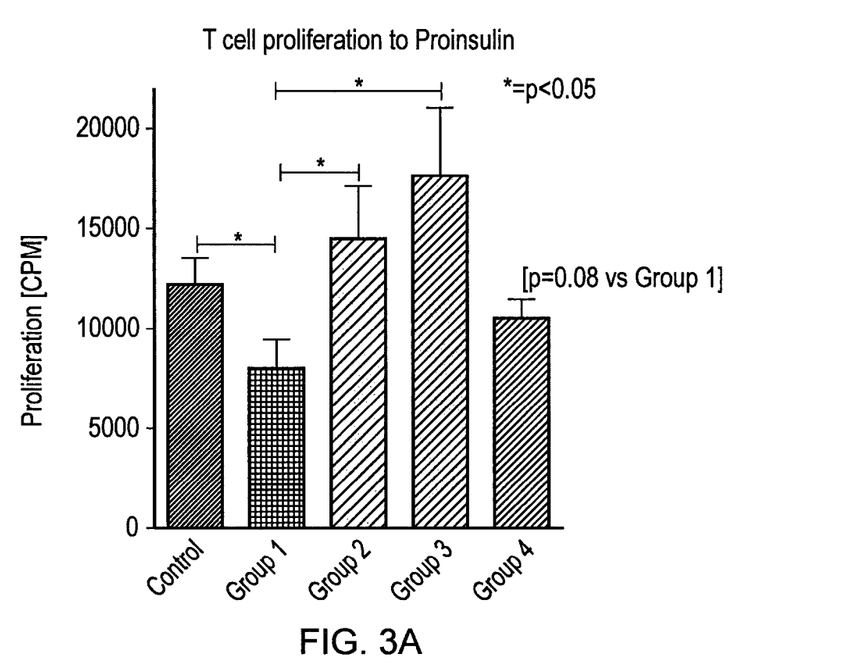
FIG. 3 shows the results of T cell proliferation as a read-out of PI and IA-2 autoimmunity following treatment of autoimmune HLA-DR4 Tg mice with multi-peptide compositions.

FIG. 3A illustrates that the Group 1 combination is the only cocktail to provide a statistically significant reduction in PI autoimmunity compared with the control. The Group 1 combination is significantly better than its nearest alternative version in reducing autoimmunity. Groups 3 and 4 do not reduce autoimmunity significantly.

Figure 3B:
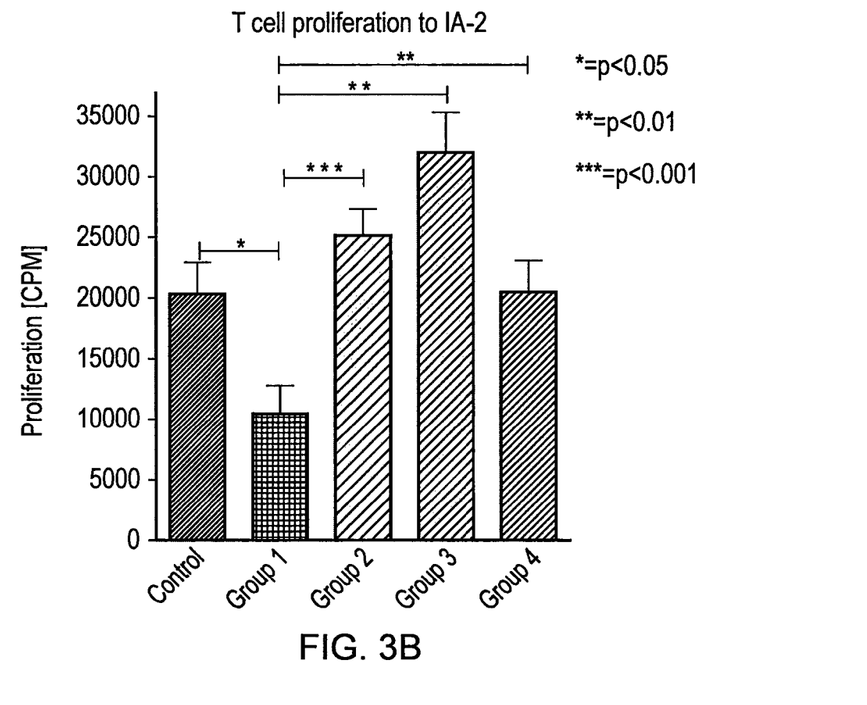

FIG. 3B illustrates that the Group 1 combination is the only cocktail to provide a statistically significant reduction in IA-2 autoimmunity compared with the control. The Group 1 combination is significantly better than its nearest alternative version in reducing autoimmunity. Groups 3 and 4 do not reduce autoimmunity significantly.

A significant reduction in proliferation (i.e. control of autoimmunity to PI and IA-2) is achieved by Group 1 peptides, which therefore show the best performance as tolerogens. It is noteworthy that Group 1-4 peptides only differ by IA-2 composition. PI peptides are the same in all Groups, yet the Group 1 peptide combination is also superior at limiting PI-specific autoimmunity. This suggests a phenomenon of trans-antigen linked suppression.

The results described above demonstrate that the presently claimed novel peptide combination is superior at limiting anti-PI and anti-IA-2 autoimmunity compared to alternative peptide combinations. Surprisingly, it has been demonstrated that different combinations of IA-2 peptides offer different effects in limiting PI autoimmunity. This is a demonstration of trans-antigen linked suppression which can be of considerable therapeutic benefit to patients. A limited number of peptides, from a limited number of auto-antigens could be used to target the multiple different auto-antigens which play a role in T1D.

EXAMPLE 7

A Specific PI Tri-Peptide Combination is More Efficacious in Limiting Pro-Insulin Autoimmunity than Each PI Peptide Alone Autoimmune responses against PI were induced in B6.129S2-H2-Ab1$^{tm1Gru}$ Tg (HLA-DRA/H2-Ea,HLA-DRB1*0401/H2-Eb) 1Kito mice (HLA-DR4-Tg) as described in Example 1 above.

Figure 4:
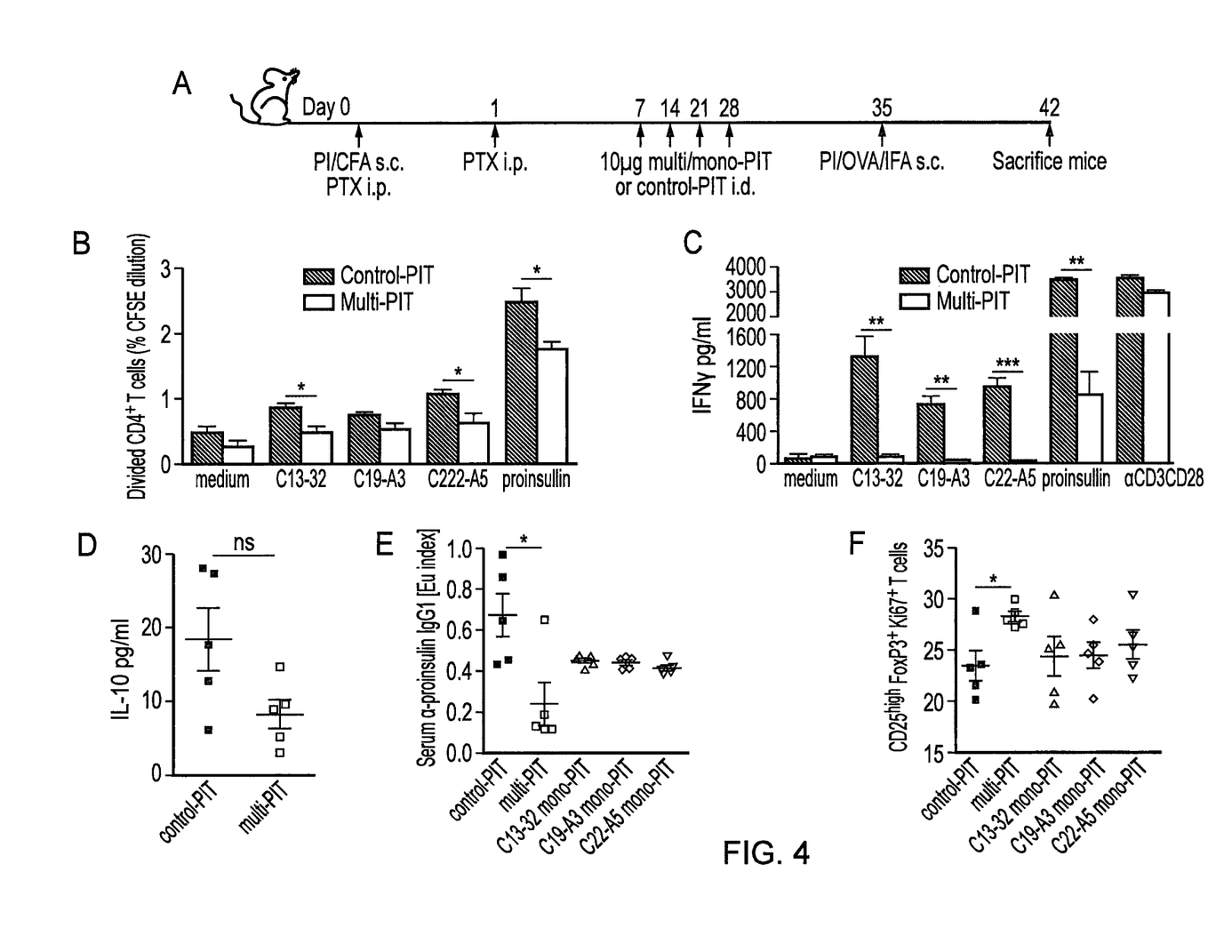

This model of PI autoimmunity was used to assess the capacity of mono- and multi-proinsulin peptides to modulate an established autoimmune response to proinsulin. The tolerogenic potential of each HLA-DR4 restricted proinsulin peptide was investigated by treating HLA-DR4-Tg mice with 4 weekly intradermal injections of mono-PI or multi-PI (an equimolar cocktail of all 3 proinsulin peptides). Recall responses were analysed in vitro, following secondary challenge with whole proinsulin-IFA to boost the ongoing autoimmune response (FIG. 4A). Multi-PI significantly down-modulated the antigen specific proliferative capacity of draining lymph nodes (DLN) cultures in response to proinsulin, and proinsulin peptides, but not ovalbumin (OVA) (FIG. 4B). In addition, multi-PI significantly decreased the synthesis of the inflammatory mediators IFN-γ, (FIG. 4C), IL-17 and IL-13 (data not shown). Interestingly, an antigen specific induction of IL-10 was not observed (FIG. 4D). Multi-PI was also effective at down-modulating the response to proinsulin protein in vivo, as indicated by reduced serum levels of proinsulin specific IgG (FIG. 4E). In contrast, mono-PI with individual C13-32, C19-A3 or C22-A5 peptides showed lower levels of therapeutic potency (FIG. 4E-F).

In relation to the mechanism of these effects, analysis of DLNs by flow cytometry demonstrated that the proportion of proliferating Tregs in the lymph nodes following multi-PI was significantly increased in comparison to control-PI treated mice (FIG. 2F). Once again, the combination of 3 proinsulin peptides was more effective than mono-PI at inducing Treg proliferation, suggesting that multiple PI peptides are more effective than single PI peptides at modulating an established autoimmune response.

EXAMPLE 8

Optimising Peptide Dosage and Administration

Figure 5:
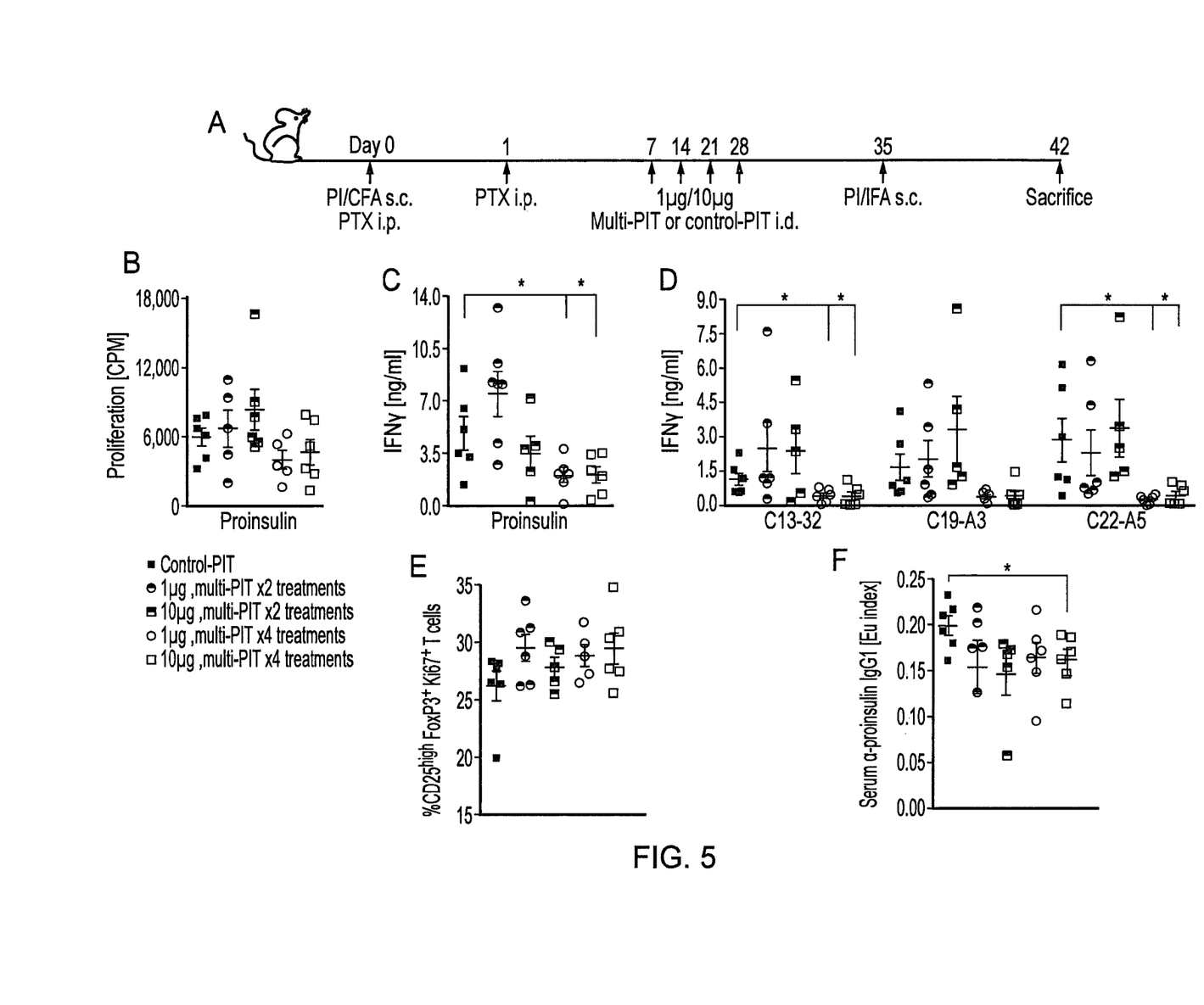

Mice were treated with either 1 or 10 μg of multi-PI, on either 2 or 4 occasions, (FIG. 5A). To establish the effect of a reduced frequency and/or dose of multi-PI, recall responses were analysed in vitro, by measuring proliferation and cytokine production of DLN cell suspensions to proinsulin protein and proinsulin peptides, (FIG. 5B-D). Reducing the number of multi-PI treatments from 4 to 2 resulted in a substantial loss of therapeutic potency. In contrast, 4 treatments of multi-PI were effective at down modulating the response to proinsulin and a reduced dose of 1 μg appeared to be as effective as 10 μg of multi-PI (FIG. 5B-D). Analysis of DLN composition by flow cytometry, at 7 days post-secondary immunisation, revealed an increased level of regulatory T cell proliferation in mice that had received multi-PI in comparison to mice that had received control-PI, with no significant difference observed between treatment groups (FIG. 5E). Proinsulin specific serum IgG levels were down modulated by multi-PI and were significantly reduced in mice that had received 4 treatments of 10 μg multi-PI (FIG. 5F).

EXAMPLE 9

Treatment With Three PI Peptides Enhances Antigen Specific Regulation

Figure 6:
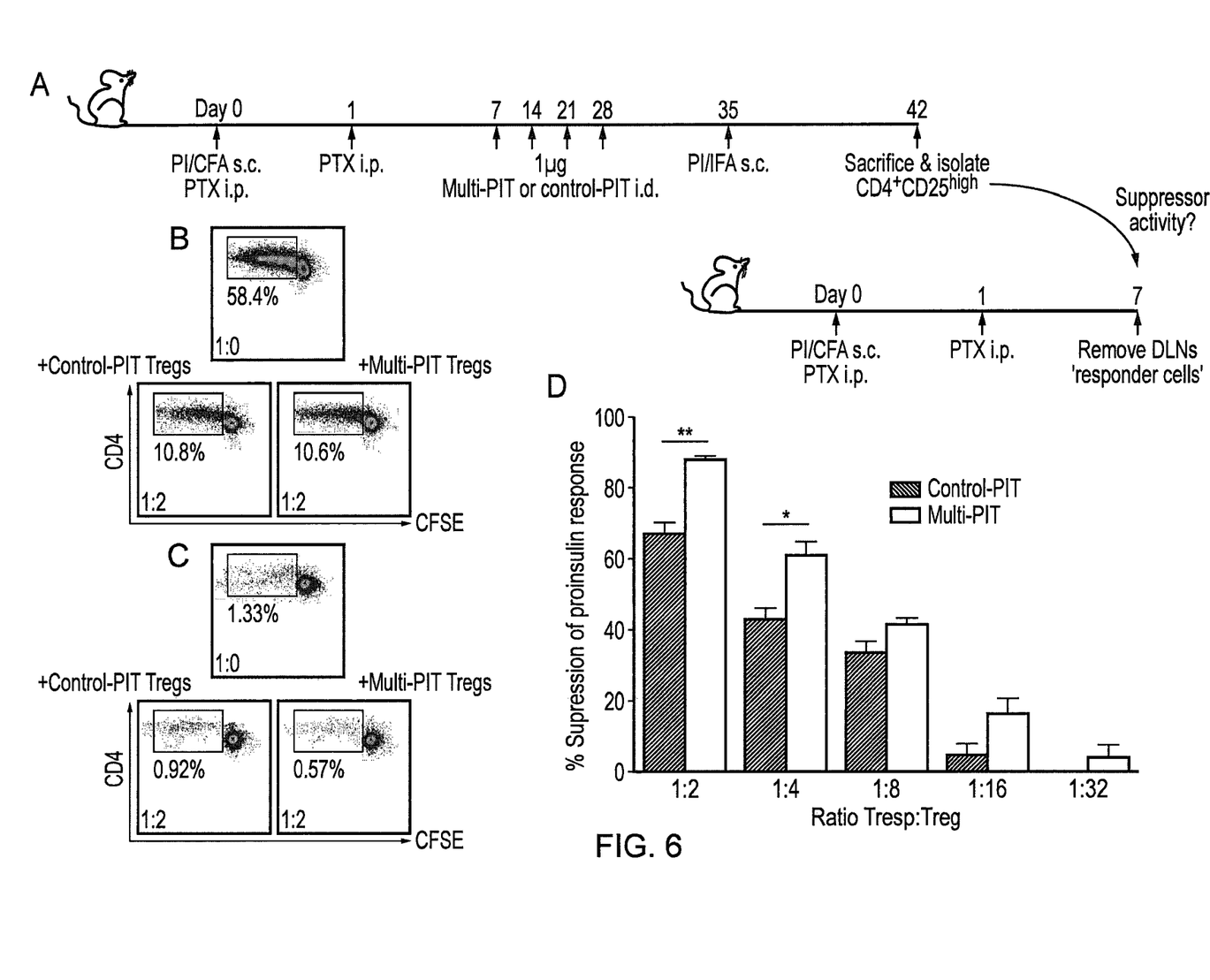

The impact of multi-PI on Treg function by measuring proinsulin specific suppressor activity in the Treg compartment of mice treated with control-PI compared to those receiving active treatment was assessed. $CD4^+CD25^{high}$ regulatory T cells were isolated from mice treated with control-PI or proinsulin multi-PI and co-cultured, at varying concentrations, with CFSE labelled responder T cells from mice immunised with proinsulin/CFA (FIG. 6A). Cells were co-cultured in the presence of anti-CD3/anti-CD28 immunomagnetic beads to measure the capacity of control-PIT and multi-PIT Tregs to suppress a polyclonal response. Tregs generated under both treatment conditions demonstrated equivalent suppressive capacity (FIG. 6B). However, in co-cultures stimulated with proinsulin protein there was distinct treatment-related suppressive capacity (FIG. 6C). Tregs from multi-PI treated mice suppressed proinsulin-specific responses to a significantly greater degree than Tregs from control-PI treated mice (FIG. 6D).

All patent and literature references cited in the present specification are hereby incorporated by reference in their entirety.

The invention claimed is:

1. A peptide combination comprising:
   an isolated peptide consisting of the amino acid sequence of SEQ ID NO: 1;
   an isolated peptide consisting of the amino acid sequence of SEQ ID NO: 2;
   an isolated peptide consisting of the amino acid sequence of SEQ ID NO: 3;
   an isolated peptide consisting of the amino acid sequence of SEQ ID NO: 4;
   an isolated peptide consisting of the amino acid sequence of SEQ ID NO: 5; and
   an isolated peptide consisting of the amino acid sequence of SEQ ID NO: 6.

2. A The peptide combination of claim 1, consisting of:
   the isolated peptide consisting of the amino acid sequence of SEQ ID NO: 1;
   the isolated peptide consisting of the amino acid sequence of SEQ ID NO: 2;
   the isolated peptide consisting of the amino acid sequence of SEQ ID NO: 3;
   the isolated peptide consisting of the amino acid sequence of SEQ ID NO: 4;
   the isolated peptide consisting of the amino acid sequence of SEQ ID NO: 5; and
   the isolated peptide consisting of the amino acid sequence of SEQ ID NO: 6.

3. A pharmaceutically acceptable composition comprising the peptide combination of claim 1 and one or more pharmaceutically acceptable excipients.

4. The pharmaceutically acceptable composition of claim 3, further comprising cysteine.

5. A method comprising administering a therapeutically effective amount of the pharmaceutically acceptable composition of claim 3 to a subject in need thereof.

6. A method for manufacturing a medicament for treatment of Type 1 Diabetes (T1 D), the method comprising formulating the pharmaceutically acceptable composition of claim 3 to be delivered by parenteral, oral or topical routes.

7. The pharmaceutically acceptable composition of claim 3 wherein the composition is formulated to be delivered by parenteral, oral or topical routes.

8. The pharmaceutically acceptable composition of claim 7 wherein the composition is formulated to be delivered by an intradermal route.

9. A method for treatment of Type 1 Diabetes (T1 D) comprising administering a therapeutically effective amount of the pharmaceutically acceptable composition of claim 3 to a patient with T1D or a non-diabetic individual identified as being at high-risk of T1 D.

10. The method of treatment of claim 9 wherein the patient has beta cell mass remaining.

11. The method of claim 9 wherein the administering includes administering via parenteral, oral or topical routes.

12. The method of claim 11 wherein the administering includes administering via an intradermal route.

13. A kit for treating Type 1 Diabetes (T1 D) comprising the peptide combination of claim 1.

14. A method of diagnosis or determining treatment efficacy comprising:
   (a) providing CD4 lymphocytes from an individual suspected of having or being susceptible to T1D;
   (b) providing a population of Antigen Presenting Cells (APCs) which bear on their surface a class II MHC molecule of an allele identical to one expressed by said individual, the population of APCs having been contacted with the peptide combination of claim 1 and the class II MHC molecule being bound to one or more of the isolated peptides 1; or (c) providing a soluble peptide-HLA multimer reagent comprising class II MHC molecules of an allele identical to one expressed by said individual, the MHC molecules having been bound to one or more isolated peptides;

(d) contacting the population of APCs of (b) or the peptide-HLA multimer of (c) with the CD4 lymphocytes of (a); and (e) determining whether the CD4 lymphocytes recognize the class II MHC-bound peptide, as an indication that the individual has, or is, susceptible to T1D.

15. The method according to claim 14 further comprising administering the peptide combination to the individual when the CD4 lymphocytes recognize the class II MHC-bound peptide.

16. A method of treatment of Type 1 Diabetes (T1D), comprising administering a therapeutically effective amount of the peptide combination of claim 1 to a patient with T1D or a non-diabetic individual identified of being at high-risk of T1D at least once per month.

17. The method of claim 16 wherein the administering is performed at least once every 2 to 4 weeks for four administrations.

18. The method of claim 16 wherein the administering is performed at least once per month.

19. The method of claim 16 wherein the administering includes administering the peptide combination at a dosage of 240 μg total peptide.

20. The method of claim 16 wherein the administering includes administering the peptide combination at a dosage of 12 mg total peptide.

21. The method of claim 16 wherein the peptide combination is formulated as a pharmaceutically acceptable composition which includes one or more pharmaceutically acceptable excipients.

22. The method of claim 21 wherein the peptide composition is formulated to be delivered by parenteral, oral or topical routes.

23. The method of claim 22 wherein the peptide composition is formulated to be delivered by an intradermal route.

24. The pharmaceutically acceptable composition of claim 7, wherein the composition is formulated to be delivered by intravenous, intradermal, intramuscular, subcutaneous, intraperiotneal, nasal, oral or epicutaneous routes.

* * * * *

SEQUENCE LISTING

```
<160> NUMBER OF SEQ ID NOS: 12

<210> SEQ ID NO 1
<211> LENGTH: 19
<212> TYPE: PRT
<213> ORGANISM: Homo sapiens

<400> SEQUENCE: 1

Ala Tyr Gln Ala Glu Pro Asn Thr Cys Ala Thr Ala Gln Gly Glu Gly
1               5                   10                  15

Asn Ile Lys

<210> SEQ ID NO 2
<211> LENGTH: 24
<212> TYPE: PRT
<213> ORGANISM: Homo sapiens

<400> SEQUENCE: 2

Lys Leu Lys Val Glu Ser Ser Pro Ser Arg Ser Asp Tyr Ile Asn Ala
1               5                   10                  15

Ser Pro Ile Ile Glu His Asp Pro
            20

<210> SEQ ID NO 3
<211> LENGTH: 13
<212> TYPE: PRT
<213> ORGANISM: Homo sapiens

<400> SEQUENCE: 3

Tyr Leu Lys Asn Val Gln Thr Gln Glu Thr Arg Thr Leu
1               5                   10
```

<210> SEQ ID NO 4
<211> LENGTH: 20
<212> TYPE: PRT
<213> ORGANISM: Homo sapiens

<400> SEQUENCE: 4

Gly Gly Gly Pro Gly Ala Gly Ser Leu Gln Pro Leu Ala Leu Glu Gly
1               5                   10                  15

Ser Leu Gln Lys
            20

<210> SEQ ID NO 5
<211> LENGTH: 18
<212> TYPE: PRT
<213> ORGANISM: Homo sapiens

<400> SEQUENCE: 5

Gly Ser Leu Gln Pro Leu Ala Leu Glu Gly Ser Leu Gln Lys Arg Gly
1               5                   10                  15

Ile Val

<210> SEQ ID NO 6
<211> LENGTH: 17
<212> TYPE: PRT
<213> ORGANISM: Homo sapiens

<400> SEQUENCE: 6

Gln Pro Leu Ala Leu Glu Gly Ser Leu Gln Lys Arg Gly Ile Val Glu
1               5                   10                  15

Gln

<210> SEQ ID NO 7
<211> LENGTH: 13
<212> TYPE: PRT
<213> ORGANISM: Homo sapiens

<400> SEQUENCE: 7

Ala Tyr Gln Ala Glu Pro Asn Thr Cys Ala Thr Ala Gln
1               5                   10

<210> SEQ ID NO 8
<211> LENGTH: 15
<212> TYPE: PRT
<213> ORGANISM: Homo sapiens

<400> SEQUENCE: 8

Tyr Leu Lys Asn Val Gln Thr Gln Glu Thr Arg Thr Leu Thr Gln
1               5                   10                  15

<210> SEQ ID NO 9
<211> LENGTH: 24
<212> TYPE: PRT
<213> ORGANISM: Homo sapiens

<400> SEQUENCE: 9

Leu Ala Lys Glu Trp Gln Ala Leu Cys Ala Tyr Gln Ala Glu Pro Asn
1               5                   10                  15

Thr Cys Ala Thr Ala Gln Gly Glu
            20

<210> SEQ ID NO 10

```
<211> LENGTH: 15
<212> TYPE: PRT
<213> ORGANISM: Homo sapiens

<400> SEQUENCE: 10

Leu Lys Asn Val Gln Thr Gln Glu Thr Arg Thr Leu Thr Gln Phe
1               5                   10                  15

<210> SEQ ID NO 11
<211> LENGTH: 28
<212> TYPE: PRT
<213> ORGANISM: Homo sapiens

<400> SEQUENCE: 11

Leu Ala Lys Glu Trp Gln Ala Leu Cys Ala Tyr Gln Ala Glu Pro Asn
1               5                   10                  15

Thr Cys Ala Thr Ala Gln Gly Glu Gly Asn Ile Lys
            20                  25

<210> SEQ ID NO 12
<211> LENGTH: 20
<212> TYPE: PRT
<213> ORGANISM: Homo sapiens

<400> SEQUENCE: 12

Ser Phe Tyr Leu Lys Asn Val Gln Thr Gln Glu Thr Arg Thr Leu Thr
1               5                   10                  15

Gln Phe His Phe
            20
```